(12) United States Patent
Morris et al.

(10) Patent No.: US 7,378,281 B2
(45) Date of Patent: May 27, 2008

(54) PROCESS TO MEASURE PPB LEVELS OF DISSOLVED COPPER IN JET FUELS AND OTHER NON-AQUEOUS FLUIDS USING A COLORIMETRIC PROCESS

(75) Inventors: Robert E Morris, Silver Spring, MD (US); Qin Lu, Alexandria, VA (US); Gregory E Collins, Huntingtown, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 844 days.

(21) Appl. No.: 10/354,990

(22) Filed: Jan. 31, 2003

(65) Prior Publication Data

US 2003/0166292 A1 Sep. 4, 2003

Related U.S. Application Data

(60) Provisional application No. 60/362,538, filed on Mar. 8, 2002.

(51) Int. Cl.
*G01N 33/20* (2006.01)

(52) U.S. Cl. .................... 436/80; 422/61; 436/73; 436/76; 436/166; 436/172; 436/182

(58) Field of Classification Search .............. 422/61; 436/73, 76, 80, 166, 172, 182–183
See application file for complete search history.

(56) References Cited

U.S. PATENT DOCUMENTS

| 4,203,725 | A | * | 5/1980 | Snowden et al. | 436/60 |
|---|---|---|---|---|---|
| 4,528,159 | A | * | 7/1985 | Liston | 422/65 |
| 4,720,374 | A | * | 1/1988 | Ramachandran | 422/310 |
| 4,755,054 | A | * | 7/1988 | Ferree | 356/418 |
| 4,930,898 | A | * | 6/1990 | Miller-Ihli | 366/109 |
| 5,223,715 | A | * | 6/1993 | Taylor | 250/343 |
| 5,304,492 | A | * | 4/1994 | Klinkhammer | 436/52 |
| 5,308,773 | A | * | 5/1994 | Lewis et al. | 436/73 |
| 5,418,615 | A | * | 5/1995 | Doyle | 356/436 |
| 5,472,878 | A | * | 12/1995 | Lewis et al. | 436/61 |
| 6,372,509 | B1 | * | 4/2002 | Foerster et al. | 436/80 |
| 6,617,588 | B1 | * | 9/2003 | Sato | 250/455.11 |

OTHER PUBLICATIONS

Ansbacher, S. et al, Industrial and Engineering Chemistry, Analytical Edition 1931, 3, 314-317.*
Short, G. H. et al, National Petroleum News 1939, 31, 162-163R.*
Livingstone, J. K. et al, Analytical Chemistry 1953, 25, 1917-1918.*
Hackett, C. E. S., Analytical Chimica Acta 1955, 12, 358-362.*
Zall, D. M. et al, Analytical Chemistry 1957, 29, 88-90.*
Howard, J. M. et al, Analytical Chemistry 1963, 35, 1016-1017.*
van Duin, H. et al, Netherlands Milk and Dairy Journal 1963, 17, 323-333.*
Strunk, D. H. et al, Journal of the Association of Official Agricultural Chemists 1965, 48, 478-482.*
Becker, R. S. et al, Journal of Physical Chemistry 1965, 69, 1435-1436.*
Gere, D. R. et al, Separation Science 1968, 3, 307-308.*
Lambdin, C. E. et al, Analytical Chemistry 1968, 40, 2196-2197.*
Deck, R. E. et al, Journal of the American Oil Chemists' Society 1970, 47, 126-128.*

(Continued)

*Primary Examiner*—Arlen Soderquist
(74) *Attorney, Agent, or Firm*—John J. Karasak; Joseph T. Grunkemeyer

(57) ABSTRACT

A method of measuring the concentration of metal ions in a sample comprising the steps of: providing a sample comprising a nonpolar, liquid hydrocarbon, suspected of containing a metal ion; adding a dye such as a spirobenzopyran dye or bathocuproine and a reducing agent to the sample; wherein the dye forms a complex with the metal ion; wherein the complex has a spectral shift in light absorbance relative to the dye; observing the spectral shift; and calculating the concentration of the metal ion in the sample.

30 Claims, 5 Drawing Sheets

OTHER PUBLICATIONS

Yoshida, H. et al, Chemical Abstracts 1971, 75, abstracts 34036e.*
Timmen, H. et al, Zeitschrift fuer Lebensmittel-Untersuchung und -Forschung 1973, 153, 283-288.*
Gershuns, A. L. et al, Journal of Analytical Chemistry 1076, 31, 1495-1496.*
Sanchez-Rasero, F. et al, Journal—Association of Official Analytical Chemists 1979, 62, 485-487.*
Oktawiec, M. et al, Chemica Analityczna 1986, 31, 491-494.*
Memon, M. H. et al, Analytica Chimica Acta 1987, 201, 345-350.*
Jiang, Y., Huazhong Shifan Daxue Xuebao, Ziran Kexueban 1989, 23, 69-71.*
Kasahara, I. et al, Water Research 1989, 23, 933-936.*
Zhou, J.-W. et al, Journal of Photochemistry amd Photobiology, A: Chemistry 1995, 87, 32-42.*
Du, B. et sl, Fenxi Huaxue 1994, 22, 1286.*
Toral, M. I. et al, Talanta 1997, 45, 147-153.*
Chibisov, A. K. et al, Chemical Physics 1998, 237, 425-442.*
Wojtyk, J. T. C. et al, Chemistry of Materials 2001, 13, 2547-2551.*
Collins, G. E. et al, Energy & Fuels 2002, 16, 1054-1058.*
Taylor, L. D. et al, Tetrahedron Letters 1967, 1585-1588.*
Yoshida, H. et al, Kokushikan Daigaku Kogakubu Kiyo 1969, 43-47.*
Li, W., Huaxue Shijie 1982, 23, 46-47.*
Suslick, K. S. et al, Journal of the American Chemical Society 1983, 105, 5781-5785.*
Suslick, K. S. et al, Journal of the American Chemical Society 1983, 105, 6042-6044.*
Freeman, J. E. et al, Analytica Chimica Acta 1985, 177, 121-128.*
Quinn, M. J., Chemical Abstracts 1987, 108, abstract 24312.*
Pleskach, L. I. et al, Journal of Analytical Chemistry 1988, 43, 66-68.*
Schlager, K. J., SPIE, 1990, 1318, 220-233.*
Saleh, M. I. et al, Analyst 1991, 116, 743-745.*
Fischer, R. et al, Journal of Organometallic Chemistry 1992, 427, 395-407.*
Huang, Q. et al, Sichuan Daxue Xuebao, Ziran Kexueban 1994, 31, 532-535.*
Prodromidis, M. I. et al, Talanta 1994, 41, 1645-1649.*
Fedorova, O. V. et al, Russian Journal of General Chemistry, 1995, 65, 591-592.*
Cole-Parmerinstrument Company Catalog 1995 pp. 542-546 and 1259-1260.*
Pande, S. G. et al, Energy & Fuels 1997, 11, 1019-1025.*
Dhas, N. A. et al, Chemistry of Materials 1998, 10, 1446-1452.*
Perez-Cid, B. et al, Analytica Chimica Acta 1998, 360, 35-41.*
Perez-Cid, B. et al, Fresenius' Journal of Analytical Chemistry 1999, 363, 667-672.*
Lagha, A. et al, Analusis 1999, 27, 452-457.*
Capelo, J. L. et al, Talanta 1999, 50, 905-911.*
Rocha, F. R. P. et al, Fresenius' Journal of Analytical Chemistry 2001, 370, 22-27.*
Hardcastle, J. L. et al, Analyst 2001, 126, 2025-2031.*
Lambdin, C. E. et al, Analytical Chemistry 1968, 40, 2196-2197.*
Lehrmann, R. et al, Process Control and Quality 1993, 4, 139-154.*
Eriksen, J. et al, Soil Biology & Biochemistry 1995, 27, 1005-1010.*
Lu, Y. et al, Journal of Geochemical Exploration 1995, 55, 49-53.*
Lavilla, I. et al, International Journal of Environmental Analytical Chemistry 1998, 72, 47-57.*
Chmilenko, F. A. et al, Ukrainskii Khimicheskii Zhurnal 1998, 64, 134-140.*
Kharisov, B. I. et al, Journal of Coordination Chemistry 1999, 47, 135-143.*
Tu, S.-P. et al, Preprints—American Chemical Society, Division of Petroleum Chemistry 1999, 44, 209-212.*
Tu, S. P. et al, Energy & Fuels 2000, 14, 1168-1175.*
Itagaki, M. et al, Journal of Electroanalytical Chemistry 2001, 504, 96-103.*
Farina, M. P. W., FSSA Journal 1981, 39-41.*
Driscoll, R. C. et al, Clinical Chemistry 1983, 29, 1609-1615.*
Knysh, P. et al Symposium Papers—Institution of Chemical Engineers, North Western Branch 1985, 7.1-7.9.*
Mann, R. et al, Institution of Chemical Engineers Symposium Series 1988, 108, 49-62.*
Taylor, D. B. et al, Journal of Chromatography 1994, 659, 133-141.*
David, P. et al, Proceedings of the International Conference on Stability and Handling of Liquid Fuels, 6th, Vancouver, B. C., Oct. 13-17, 1997 (1998), vol. 1, 171-184, Editor: Giles, Harry N., Publisher: National Technical Information Service, Springfield, VA.*
Hagenson, L. C. et al, Chemical Engineering Science 1998, 53, 131-148.*
Hanby, J. D. Environmental Science Research 1996, 51, 401-407.*
Collins et al., "Photoinduced Switching of Metal Complexation by Quinolinospiropyranindolines in Polar Solvents", Chemistry Communication., 1999, 321-322.
Winkler et al., "Photodynamic Fluorescent Metal Ion Sensors With Parts Per Billion Sensitivity", Journal of American Chemistry Society 1998, vol. 120, pp. 3237-3242.
Evans et al., "Selective Metals Determination With A Photoreversible Spirobenzopyran", Analytical Chemistry 1999, vol. 71, No. 23, pp. 5322-5327.

* cited by examiner

PROCESS TO MEASURE PPB LEVELS OF DISSOLVED COPPER IN JET FUELS AND OTHER NON-AQUEOUS FLUIDS USING A COLORIMETRIC PROCESS

This application claims priority to U.S. provisional patent application No. 60/362,583 filed on Mar. 8, 2002.

BACKGROUND OF THE INVENTION

1. Field of the Invention

The invention relates generally to spectrophotometric methods of measuring trace quantities of metals in jet fuel.

2. Description of the Prior Art

It has been well established that trace quantities of certain metals will promote autoxidation of organic compounds in the presence of oxygen. While it has been observed that iron, zinc, and lead can promote the oxidative degradation of hydrocarbon fuels, copper and its compounds have been shown to be one of the most active and available oxidation initiator instability promoters. Trace levels of dissolved copper (typically 25 µg/L or less) can greatly accelerate the rate and extent of autoxidation in fuels. It is generally believed that catalytic metals or surfaces such as copper initiate free-radical autoxidation through the catalytic formation of hydroperoxy radicals.

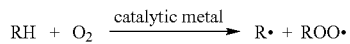

In addition, copper can catalyze the decomposition of hydroperoxides to generate additional free radicals through the following mechanisms

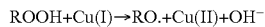

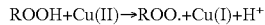

Because dissolved copper can operate as both a reducing agent (Cu(I)) and an oxidizing agent (Cu(II)), very low concentrations of copper can cause the rapid decomposition of large amounts of hydroperoxides.

Despite the fact that the copper sweetening process has been almost entirely replaced by processes such as Merox treating and hydrotreating that do not introduce copper contamination, copper can still be acquired by jet fuel from contact with copper-bearing alloys in fuel handling processes, including pipes, brass fittings, bearings, and most significantly, Navy shipboard fuel handling systems which are comprised largely of Cu/Ni admiralty metal. Unfortunately, these low levels of dissolved copper in jet fuel promote oxidation degradation that often leads to the formation of gums and sediments in aircraft fuel systems, thereby impeding engine performance, and exerting a significant impact on maintenance costs. In gas-drive fuel Coker tests, as little as 15 to 25 µg/L of added copper or iron, and 100 to 250 µg/L of added zinc or lead were shown to have deleterious effects on JP-7 thermal stability. There is also evidence that dissolved copper can promote certain prerequisite chemical reactions in jet fuel during storage, which enhance the autoxidation process and result in further thermal degradation.

In a shipboard JP-5 fuel survey conducted by Southwest Technical Institute, out of over 200 samples, the copper ranged between 0 and 838 µg/L, with approximately 10% of the samples containing more than 50 µg/L. The majority of the fleet fuel samples tested were found to fail the standard JFTOT test for thermal stability when they contained 50 µg/L of dissolved copper, and several samples failed with 25 to 50 µg/L copper. Some fuels failed the JFTOT test with as little as 15 µg/L copper, although it is generally agreed that levels above 25 µg/L should be avoided.

The determination of copper in fuel to this level is nontrivial. Graphite furnace-atomic absorption spectroscopy analysis is currently the only method available to reliably quantify copper in fuel at these low levels. Thus, there is no field method currently available to detect low threshold levels of dissolved copper in jet fuel. While there are numerous metallochromic spectrophotometric methods for quantitating copper levels in aqueous media, there have been no reports to date dealing with the direct application of these dyes to fuels.

SUMMARY OF THE INVENTION

The invention comprises a method of measuring the concentration of metal ions in a sample comprising the steps of: providing a sample comprising a nonpolar, liquid hydrocarbon, suspected of containing a metal ion; adding a dye to the sample such as a spirobenzopyran dye or bathocuproine and a reducing agent; where the dye forms a complex with the metal ion having a spectral shift in light absorbance relative to the dye; observing the spectral shift; and calculating the concentration of the metal ion in the sample.

DETAILED DESCRIPTION OF THE PREFERRED EMBODIMENTS

Figure 1:
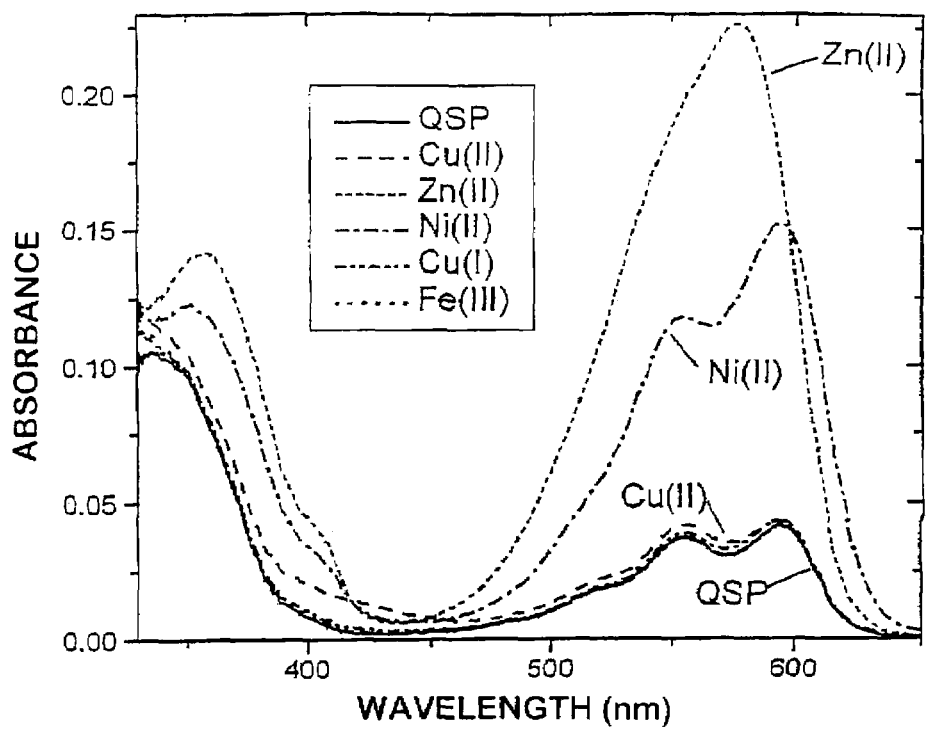
FIG. 1 shows the spectrophotometric response of QSP in Jet A jet fuel with 20% ethanol to the addition of 300 µg/L Cu(II), Zn(II), Ni(II), Cu(I), and Fe(III)

The first step in the method of the invention is providing a sample of a nonpolar, liquid hydrocarbon, suspected of containing a metal ion. The sample may comprise jet fuel, which is usually made up of alkanes. The metal ion may be Cu(I), Cu(II), or combinations of these or other metal ions. Bathocuproine (BCP) is highly selective for Cu(I). The spirobenzopyran dyes may be used for copper or for other metal ions.

Although it is generally believed that Cu(II) is the primary culprit in the oxidation degradation of hydrocarbon fuels, Cu(I) can also play an important role in this process. While Cu(I) is recognized as being very unstable in aqueous solution, $K=[Cu(II)]/[Cu(I)]^2 \approx 10^6$, the relative stability of Cu(I)/Cu(II) depends very strongly on the type of anions or ligands present in solution. In jet fuel, the possible presence of sulfur containing ligands or other ligands that favor the formation of tetrahedral copper coordination complexes could stabilize the Cu(I) oxidation state, making the Cu(I) concentration in jet fuel a quantifiable fraction of the total copper content.

The sample may contain a metal deactivating additive (MDA). MDA's are occasionally added to jet fuel in order to help prevent any thermal problems associated with copper contamination. MDA deactivates the catalytic activity of copper because the MDA-Cu complex formed forces the copper into a square planar geometry in which d-orbital electron transfer reactions are no longer favored. However, in a tetrahedral configuration, Cu(I) is still capable of electron transfer and, therefore, remains catalytically active.

In the next step, a dye is added to the sample. The dye is one that forms a complex with the metal ion, which has a spectral shift in light absorbance relative to the dye. The term shift includes movement of an absorption peak to another wavelength, appearance of a new peak, and disappearance of a peak. Suitable dyes include spirobenzopyran dyes, quinolinospiropyranindoline (QSP), nitroquinolinospiropyranindoline (NQSP), and BCP. When the dye is BCP, a reducing agent is also added to the sample. Suitable reducing agents include, but are not limited to, ascorbic acid. The reducing agent reduces Cu(II) to Cu(I), which is the BCP complexing form.

Some dyes may not be suitably soluble in the sample. The solubility may be improved by the addition of a polar, organic solvent such as ethanol. The solvent may be added directly to the sample, or the dye may be dissolved in the solvent before addition to the sample. A suitable concentration of ethanol in the sample may be at least about 2% and up to about 20%.

Spirobenzopyran dyes are a class of metal complexation indicators, which have been shown to exhibit extremely sensitive absorptivity changes following complexation of transition metal ions. These dyes undergo photoreversible spectral shifts that are unique for different metal ions. Moreover, their performance is enhanced in nonaqueous solvents. Absorption spectroscopy is very amenable to field implementation, although it is typically hampered by low sensitivities (mg/L, parts per million regime). Some spirobenzopyran metal complexes, however, have high molar absorptivities for the metal complexes formed. The general structure of spirobenzopyrans is shown below. Q may be a Lewis base such as oxygen, sulfur, or nitrogen.

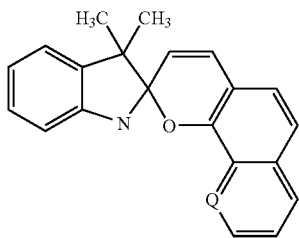

NQSP and QSP differ structurally only in the covalent attachment of a nitro functional group para to the phenolate ion for NQSP, as shown below.

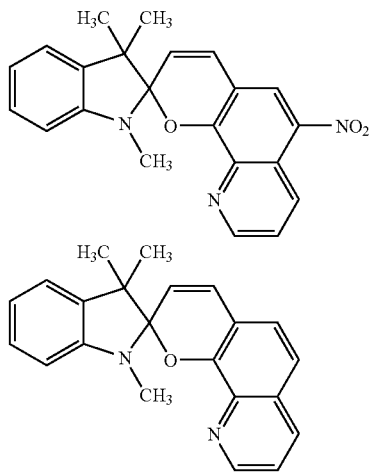

These dyes have significantly different solubility and color change responses to metal complexation. Colorimetric changes observed are from colorless to red for QSP and violet to red for NQSP upon exposure to Cu(II). NQSP complexes different metal ions with distinctly different spectroscopic signatures in the visible wavelength region. Although there is overlap of the absorbance spectra for various NQSP-metal complexes, partial least-squares analysis has been successfully used to selectively identify six different transition metal ions in the plasticizer solvent, dicapryl phthalate, in both single and binary component mixtures. NQSP has enabled the detection of copper in the presence of low levels of interferents such as nickel and zinc. In a survey of various jet fuel samples, the highest zinc and iron concentrations found were 30 and 16 µg/L, respectively, while the majority of fuel samples had undetectable levels. Nickel concentrations, on the other hand, from exposure to copper-nickel piping, were as high as 52 µg/L, with one sample containing 170 µg/L. Selective detection of copper in the presence of these metal interferents is a critical issue to the application of any indicator dye. NQSP and QSP have demonstrated improved spectroscopic behavior in non-aqueous solvents, e.g., benzene, tetrahydrofuran, acetonitrile, and dicapryl phthalate, indicating the applicability of these dyes to jet fuel, a characteristic certainly not common for most aqueous based indicator dyes.

QSP and NQSP are solvatochromic dyes that are extremely sensitive to polarity, responding to the addition of ethanol with an equilibrium shift of the molecule from a spirobenzopyran or "closed" state to a merocyanine or "open" isomeric state. These states correspond to the breaking and forming of a phenolate bond within the molecule. The merocyanine form opens the molecule up, exposing the phenolate anion and dramatically improving metal complexation, while the spirobenzopyran state removes this binding site, effectively eliminating the metal binding capabilities of this molecule. QSP, when dissolved in pure jet fuel, is nearly colorless. This is a direct indication that the spirobenzopyran-merocyanine equilibrium for QSP has shifted to the colorless spirobenzopyran isomer due to the nonpolar character of this medium. Under these conditions, metal binding of Cu(II) requires a shift in the equilibrium to the merocyanine form, a condition that is not favored until the addition of a polar solvent such as ethanol. NQSP, in contrast, equilibrates to a significantly higher fraction of merocyanine dye following the addition of only 2% ethanol. The reason for this is the presence of the nitro functional group, which sufficiently stabilizes the phenolate anion. In this way, NQSP is significantly more sensitive to Cu(II) in the presence of minimal amounts of ethanol (the sensitivity of NQSP at 440 nm for Cu(II) is nearly 2.5 times more sensitive than QSP at 425 nm, for example), and more importantly, the baseline spectrum of NQSP in the absence of any metal ions is significantly less sensitive than QSP to slight polarity changes, a feature which should make quantitation more straightforward.

BCP and its water soluble derivative bathocuproinedisulfonate (BCS) are well known reagents used for the spectrophotometric determination of Cu(I), or total copper concentration in the presence of a suitable reducing reagent. These analyses are typically carried out in aqueous media, such as seawater, drinking water, and/or rainwater. Alternatively, there are several reports of BCP being applied to the liquid extraction of copper into an organic phase solvent, e.g., 1,2-dichloroethane, for subsequent spectrophotometric determinations. There are no reported applications in which BCP has been utilized either directly or indirectly for the measurement of dissolved copper in fuels. The structure of BCP is shown below.

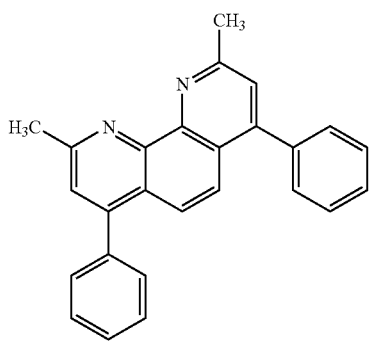

In the next step, any spectral shift caused by the complexation is observed. This may be done using any spectrophotometer that can detect spectra in the relevant frequency range. The observing may be done by measuring the absorbance spectrum of the sample after the adding step, and comparing this spectrum to one or more other spectra. The comparison spectra may include that of the original sample, the dye, the dye dissolved in the solvent, the complex, and a sample known to be free of the metal ion.

Real-world fuel samples may vary in their dielectric properties, and levels of absorbing chromophores (color bodies), MDA, copper, and other metals. Each of these parameters will ultimately influence the baseline absorbance of the dye, affecting the quantitative capability of the dye. By removing all of the dissolved copper from a given jet fuel sample, a reference sample is obtained, which upon the addition of the dye, will best represent the spectroscopic behavior of the dye in the jet fuel in the absence of any copper contamination. This reference spectrum can then be utilized to correct each of the spectra recorded in a typical standard addition method.

The final step is to calculate the concentration of the metal ion in the sample. The spectra are the basis of the calculation. A variety of methods including, but not limited to, principle component analysis and partial least-square analysis may be used.

Bathocuproine (BCP, 2,9-dimethyl-4,7-diphenyl-1,10-phenanthroline) is part of a class of well known phenanthroline dyes that are used in spectrophotometry. Complexation with Cu(I) causes BCP to undergo a change in absorption characteristics that can be correlated with the Cu(I) concentration. In order to determine total copper, i.e., Cu(I) and Cu(II), a suitable reducing agent is added to convert the Cu(II) to Cu(I). BCP is specific to Cu(I) and remains optically transparent in the presence of all other metals. Thus, it is not necessary to remove copper from the fuel sample, when utilizing BCP to quantify total copper.

A field test kit may be made for measuring copper concentration in a fuel sample so that samples can be tested immediately on site, without waiting for the samples to be sent to a remote test lab. The kit may involve filling a reference cell with a mixture comprising the fuel and 2.0 mM ascorbic acid and 20% ethanol. A sample cell may comprise the fuel, 1.5 mM BCP, 2.0 mM ascorbic acid, and 20% ethanol. The test sample may be sonicated by a portable microprobe sonicator for 15 minutes. A portable fiber optic spectrophotometer may measure the absorbance of the sample at 476 nm versus the reference. The data may be transmitted to a laptop PC for calculation of the copper content of the fuel. The kit may also be calibrated by measuring the absorbance of a series of samples containing standard additions of copper. The test may be completed in as little as 20 minutes. Other embodiments of a test kit may also be possible and are within the scope of the claims.

Having described the invention, the following examples are given to illustrate specific applications of the invention. These specific examples are not intended to limit the scope of the invention described in this application.

EXAMPLE 1

Measurement of metal ions in jet fuel using NQSP and QSP—NQSP was prepared by the condensation of Fisher's base 1,3,3-trimethyl-2-methyleneindoline with 7-formyl-8-hydroxy-5-nitroquinoline as described in Winkler et al., *J. Am. Chem. Soc.*, 1998, 120, 3237-3242, incorporated herein by reference. A similar synthetic procedure for QSP as described in Przystal et al., *J. Heterocyclic Chem.*, 1967, 4, 131, incorporated herein by reference. The metal salts utilized were copper(II) ethylacetoacetate (Pfaltz & Bauer), copper(I) chloride (Fischer Scientific), nickel(II) 2-ethylhexanoate (Alfa Aesar), zinc(II) 2-ethylhexanoate (Alfa Aesar), and iron(III) ethoxide (Alfa Aesar). N,N'-disalicylidene-1,2-propanediamine, the active ingredient in a widely used metal deactivating additive (MDA), was obtained from Pfaltz & Bauer. Metal complexation agent ethylenediamine tetraacetic acid, tetrasodium salt ($Na_4EDTA$) was supplied by Aldrich and diethylenetriamine bound to silica gel (DETA-Si) was prepared as described in Morris et al., *Petrol. Sci. Technol.*, 2000, 18, 1147-1159, incorporated herein by reference. Jet A and JP-5 fuels were in accordance with applicable specifications and contained less than 15 μg/L copper. All spectrophotometric results were recorded on a Hitachi U-3000 dual beam spectrophotometer. Data analysis was performed using MATLAB (version 6.1, Mathworks Inc., Natick Mass.). Principle component analysis routines were used from the PLS_toolbox (version 2.1.1, Eigenvector Technologies Inc., Manson, Wash.). Prior to chemometric analysis, the NQSP absorbance spectrum for each series was subtracted from the metal-NQSP complexation spectrum. This background subtraction was found to improve the reproducibility of the spectra.

Figure 2:
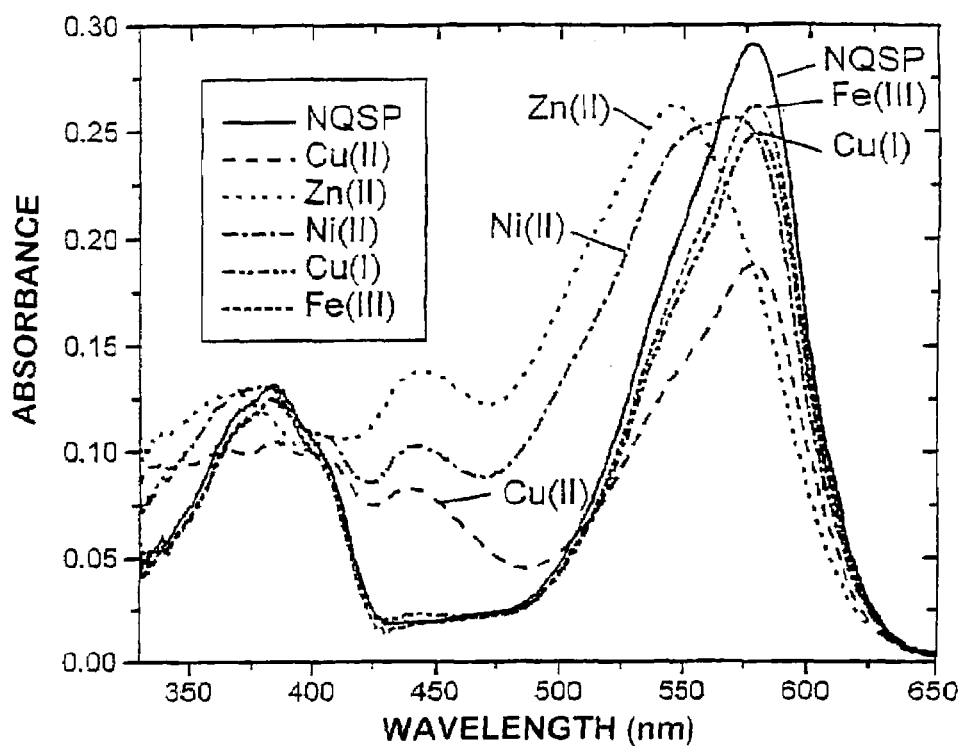
FIG. 2 shows the spectrophotometric response of NQSP in Jet A jet fuel with 2% ethanol to the addition of 300 µg/L Cu(II), Zn(II), Ni(II), Cu(I), and Fe(III).

FIGS. 1 and 2 show that the addition of various metal ions to solutions of QSP and NQSP, respectively, in Jet A resulted in extremely sensitive spectroscopic changes in the absorbance spectra. NQSP responded to the addition of Cu(II) with the formation of a blue-shifted absorbance peak at 440 nm, while the primary absorption peak at 572 nm was reduced (color change observed is from purple to red). QSP, unlike NQSP, complexed copper(II) with a small increase in the absorbance band from 525 to 625 nm and the formation of a blue-shifted absorbance peak at 425 nm, causing a color change in solution from colorless to red with the addition of Cu(II).

Figure 3:
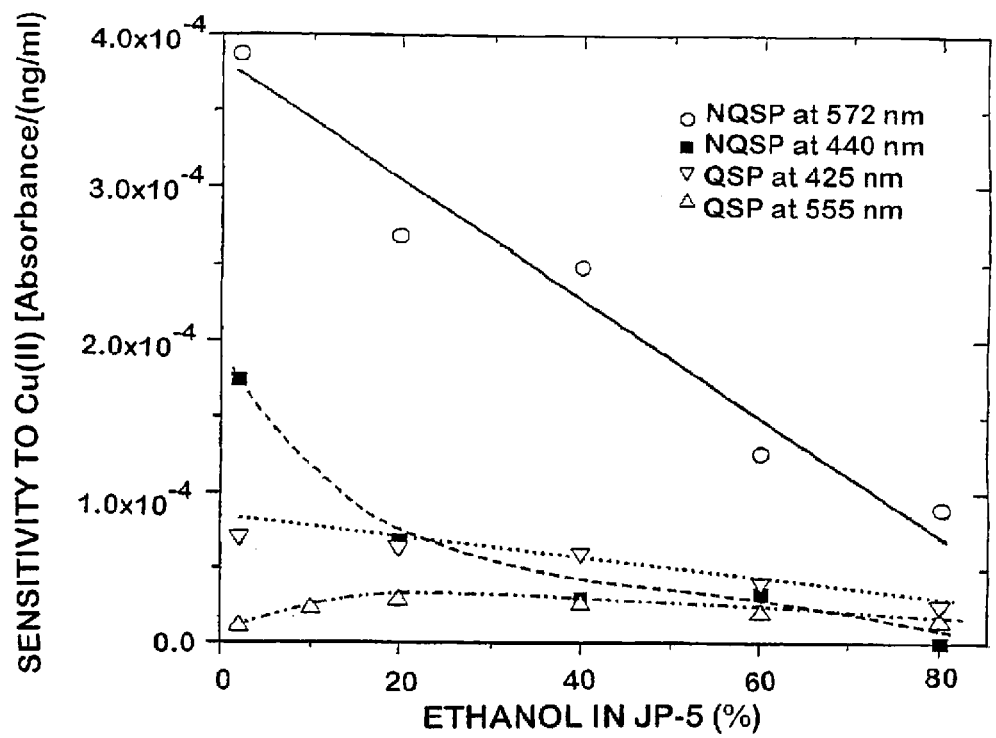
FIG. 3 shows the sensitivity of response for QSP and NQSP to Cu(II) as a function of the total ethanol concentration in JP-5 jet fuel.

NQSP and QSP were nearly insoluble in the jet fuel without the addition of at least about 2% ethanol, a quantity which was added by spiking the jet fuel sample with a concentrated aliquot of NQSP or QSP in ethanol stock solution. FIG. 3 shows that the ethanol concentration in jet fuel was a critical parameter influencing the sensitivity of NQSP and QSP in response to Cu(II). In FIG. 3, the sensitivity of QSP and NQSP to Cu(II), i.e., the slope of the absorbance change as a function of copper concentration is plotted versus increasing levels of ethanol in JP-5 jet fuel. To more accurately represent the sensitivity of this approach to an actual field application, the concentration of copper in the jet fuel sample prior to any dilution effects by the addition of ethanol/dye as a cosolvent, was utilized for all sensitivity calculations. With respect to QSP at 555 nm, the sensitivity to Cu(II) increased until the addition of approximately 20% ethanol, at which point the dilution effect resulting from the addition of ethanol forced a continual drop in sensitivity. At 425 nm, however, the addition of ethanol immediately caused a linear decrease in sensitivity to Cu(II), although the decline in sensitivity lagged behind the expected dilution effect from ethanol addition. NQSP, on the other hand, responded to the addition of ethanol to JP-5 with a continual and immediate drop in sensitivity at both 440 and 572 nm that, for the most part, was directly ascribed to a dilution effect by the added ethanol.

Figure 4:
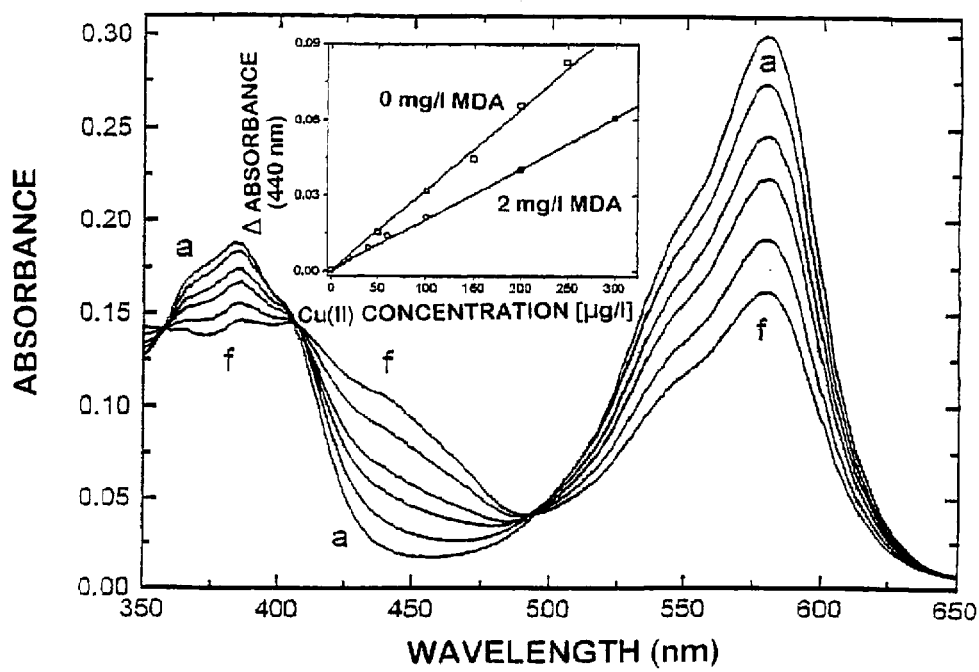
FIG. 4 shows the spectral response of NQSP in Jet A jet fuel containing 0 mg/L MDA to increasing concentrations of Cu(II) and the inset graph demonstrates the linearity of response obtained for increasing Cu(II) concentrations from 0 to 300 µg/L at 440 nm in the presence and absence of 2 mg/L MDA.

Both QSP and NQSP responded linearly and sensitively to the addition of Cu(II) in jet fuel, albeit in two different spectroscopic regions. Typical data obtained are shown in FIG. 4, which shows the response of NQSP in JP-5 fuel with 2% ethanol following the sequential addition of Cu(II). The inset plot shows the change in absorbance at 437 nm as a function of Cu(II) concentration. The detection limit for Cu(II) under these conditions, assuming a signal-to-noise ratio of 3:1, is 9.3 µg/L, or 9 ppb. Although the absorbance change occurring at 572 nm was significantly more sensitive to Cu(II) than that observed at 437 nm, defining a true baseline for this red-shifted wavelength band (spectrum for jet fuel containing 0.0 µg/L Cu(II)) following a metal ion extraction step via silica-bound diethylenetriamine was difficult.

In comparing the two spirobenzopyran dyes, NQSP and QSP, with respect to their capability for selectively and sensitively detecting trace levels of Cu(II) in jet fuel, it was found that NQSP had (1) enhanced sensitivity to Cu(II) which was nearly 2.5 times that of QSP, (2) more dynamic and unique spectral response following the addition of interfering metal ions, and (3) lower sensitivity to interfering metal ions of concern, Zn(II) and Ni(II). For each of the three primary metal ions of interest, Cu(II), Ni(II), and Zn(II), a set of seven concentrations varying from 25 to 300 µg/L were prepared in JP-5 fuel, and the spectra collected following the addition of NQSP. FIG. 2 shows that that each of these three metal ions engendered a characteristic spectrum that is unique from the other two. In the wavelength band 500 to 650 nm, there were two primary peaks at 546 and 577 nm that defined this band. Metal complexation of Zn(II) by NQSP caused a dramatic decrease in the peak at 577 nm, while enhancing the 546 nm peak. The net result was an easily measurable decrease in absorptivity and a wavelength shift of 23 nm toward the blue. For Ni(II), the peak at 546 nm was enhanced, while the peak at 577 nm was diminished slightly. Finally, metal complexation of Cu(II) by NQSP caused a significant decrease in both spectral peaks, maintaining the intensity ratio between these two peaks. In the wavelength band from 420 to 500 nm, all three metals caused an increase in absorbance at 439 nm, with only minimal spectral wavelength shifts differentiating these three metals. Finally, in the wavelength band of 330 to 425 nm, each metal ion had its own unique spectral response that further differentiates one metal complex from the other. The different spectroscopic signatures obtained by NQSP for these different metal ions indicated that the application of chemometric methodologies can successfully enable the selective identification of metal impurities found in a given jet fuel sample.

Figure 5:
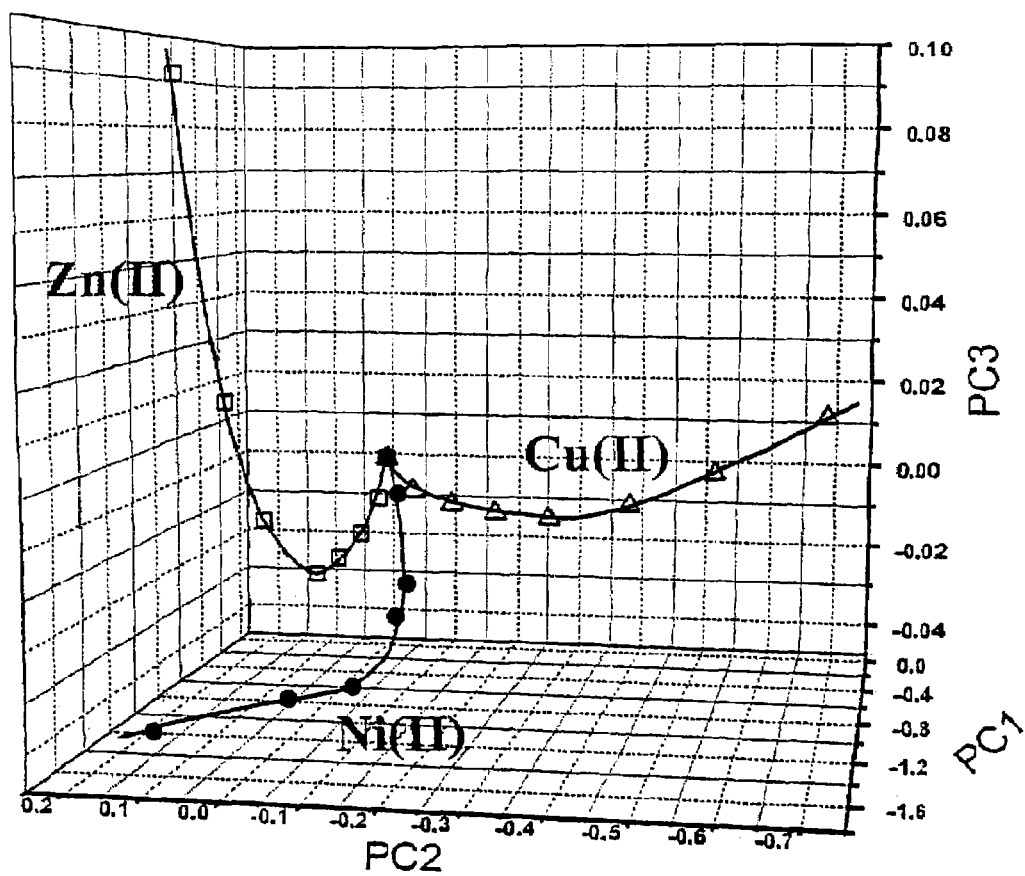
FIG. 5 shows the principal component analysis (PCA) plot for NQSP in JP-5 showing good separation between Cu(II), Zn(II), and Ni(II) at concentrations varying from 25 to 300 µg/L.

Preliminary treatment of these data by a principal component analysis (PCA) indicated that the contributions to the absorption spectra by these metals in JP-5 were readily separated with these techniques. The PCA plot for Cu(II), Zn(II), and Ni(II) (FIG. 5) shows a large separation of the different principal components (i.e., metal spectra) for each of the different concentrations examined. It is apparent that of the three metal ions examined here, the Cu(II) spectral response was most easily differentiated from the remaining two metal ions due to its orthogonal score as shown in FIG. 5.

Figure 6:
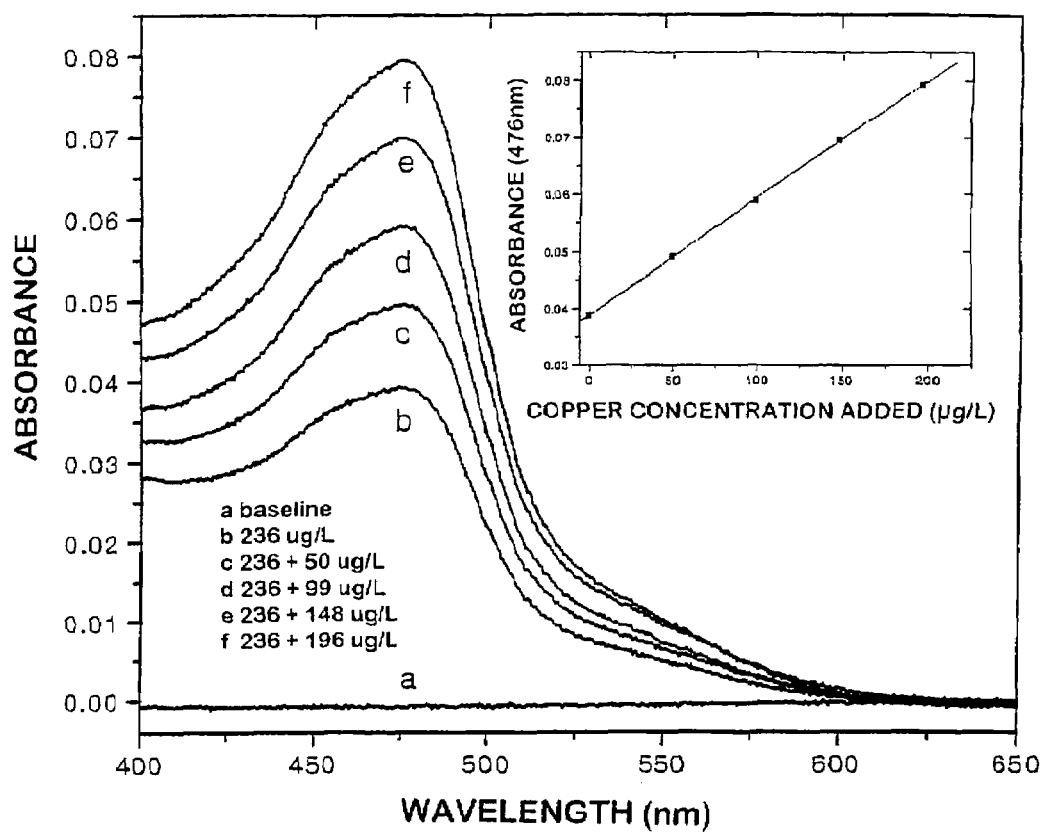
FIG. 6 shows the spectrophotometric response of BCP in shipboard JP-5 sample #02-23 with standard additions of copper and the inset shows linearity of copper response at 476 nm.

Metal-deactivating additives (MDA) are occasionally added to jet fuel in order to help prevent any thermal problems associated with copper contamination. Because MDA is simply a metal chelating agent, it was presumed that competition existed between MDA and NQSP for complexation of metal ions in jet fuel. Typical levels for MDA in jet fuels range from 0 mg/L to approximately 2 mg/L, although it is still allowed as high as 5.8 mg/L. When Jet A fuel was dosed with up to 600 µg/L of copper from copper ethylacetoacetate in the presence of 2 mg/L MDA, the absorption wavelength maximum at 439 nm was unaffected. In addition, the linearity of the NQSP response to dissolved copper was retained, although the slope was decreased by 37% (see FIG. 4). MDA was determined to have minimal impact on the NQSP baseline spectrum in Jet A in the absence of Cu(II), indicating that there was no interaction between NQSP and MDA. The decrease in sensitivity was likely associated with the incomplete extraction of copper from the copper-MDA complex. In FIG. 6, the change in NQSP-copper absorbance at 437 nm with increasing MDA concentration in a Jet A sample containing 100 µg/L Cu(II) is shown, when corrected for the absorbance signal obtained in the absence of copper. Although an easily measured absorbance change was observed for 100 µg/L copper even in the presence of 10 mg/L MDA, the change in sensitivity observed with MDA concentration complicated the quantification of copper in jet fuels containing unknown MDA concentrations.

A reference spectrum was made by removing the copper from jet fuel with the powerful sequestering agents EDTA and silica-bound diethylenetriamine (DETA-Si). Several hours were necessary for the EDTA to remove all the available copper, while the DETA-Si worked on a much faster time scale. For a Jet A sample containing 220 µg/L copper, 2% (w/v) of DETA-Si enabled the complete extraction of all the copper in less than two minutes, and the extraction of 70% of the dissolved copper in one minute. By doubling the amount of DETA-Si to 4% (w/v), a complete extraction of the copper was complete in less than one minute, demonstrating the strong adsorptivity of this extraction material.

A 50 µg/L Cu(II) in jet fuel sample was prepared and quantitatively determined by standard addition after the background spectra for NQSP with 0.0 µg/L copper was established via the solid-phase extraction of copper with DETA-Si. After four trials, the calculated concentration was 46.9 µg/L with a standard deviation of 3.0 µg/L. The detection limit for this method, based upon a signal-to-noise ratio of 3:1, was estimated to be 9.3 μg/L copper in the absence of MDA. In the presence of 2 mg/L MDA, the detection limit was estimated to be 12.7 μg/L copper.

EXAMPLE 2

Measurement of metal ions in jet fuel using BCP—Bathocuproine (BCP) was purchased from Sigma. Ascorbic acid, hydroquinone, and diethylenetriamine (DETA) were obtained from Aldrich. Cu(II) ethylacetoacetate (Cu[EA]) was obtained from Strem. The metal deactivating additive, N,N'-disalicylidene-1,2-propanediamine (MDA), was supplied by Pfaltz & Bauer. Metal compounds, Ni(II) 2-ethylhexanoate, Zn(II) ethylhexanoate, and Fe(III) ethylacetoacetate, were obtained from Alfa Aesar. Ethanol (200 Proof, anhydrous) was purchased from Warner-Graham. Copper(I) oxide and perchloric acid were obtained from Johnson Matthey and J. T. Baker, respectively.

Test fuels: Fuel studies were performed with a specification Jet-A fuel that contained no additives and had less than 8 μg/L copper by GFAA. A sample of specification JP-5 fuel was obtained that contained 8 μg/L copper by GFAA (I.D #01-21), and a portion of this fuel was contaminated with copper by exposure to copper plates to a level of 1070 μg/L (I.D. #02-01). A sample or JP-5 was also obtained from a carrier defueling operation, and GFAA showed the fuel had acquired 224 μg/L copper from normal shipboard handling (#02-23).

BCP method for the determination of total dissolved copper: The total dissolved copper content in jet fuel samples was determined spectrophotometrically by the standard addition of Cu[EA] to a jet fuel sample containing BCP, a reducing agent (i.e., ascorbic acid or hydroquinone), and ethanol. The sample solutions were prepared by dissolving solid BPC in a mixture of 10-20% ethanol containing reducing agent and 90-80% jet. fuel. The final reagent concentrations were: BCP, $1.5 \times 10^{-3}$ M; ascorbic acid or hydroquinone, $2.0 \times 10^{-3}$ M; and ethanol, 20%. Higher concentrations of BPC interfered with the baseline measurement at 476 nm, leading to inaccuracies. Five to fifteen minutes of sonication (Mettler Electronics Corp.) were necessary to aid in dissolution of the BCP and to ensure complete development of the colored Cu-BCP complex, via what is likely sonolytic liberation of copper from competing ligands in the fuel. All absorbance measurements were corrected for absorbing species in the fuel by referencing against a mixture of the fuel sample being analyzed, containing an identical concentration of ethanol and the reducing agent, but no BCP. The absorbance at 476 nm, the characteristic absorption wavelength of the Cu(I)-BCP complex, was measured with a Cary 5E dual beam spectrophotometer using a 1 cm pathlength cuvette. Nickel(II), zinc(II), and iron(II) did not interfere in the response of BCP for copper. The BCP procedure was also carried out with a portable, fiber optic spectrometer system (Ocean Optics S2000) with a tungsten halogen lamp source (ISS-2) and a 1 cm pathlength cuvette holder. The absorbance spectra were smoothed by continuously averaging three sequentially recorded spectra.

Graphite furnace atomic absorption: Copper was determined in fuel samples by graphite furnace atomic absorption in accordance with ASTM D6732, incorporated herein by reference.

Total dissolved copper determination by the BCP method: Initial experiments were carried out in a copper-free Jet-A fuel sample which was freshly doped with known amounts of Cu[EA], in order to optimize the experimental conditions. Since BCP is considered to be selective for Cu(I), it was necessary to include a suitable reducing agent to ensure that all the copper was present as Cu(I). Ascorbic acid and hydroquinone were selected as potential reducing agents on the basis of their solubility in ethanol-jet fuel mixtures and their effectiveness in reducing Cu(II) to Cu(I) in organic media. In fact, the reducing power of these compounds is actually higher in non-polar environments than in water, since polar solvents can interfere with electron transfer equilibria.

FIG. 6 shows the recorded spectra and graphical treatment of a typical standard addition experiment. For fuel samples freshly doped with Cu[EA], both the BCP-ascorbic acid and BCP-hydroquinone reagent systems gave accurate quantitation, providing linear responses to copper from 20 μg/L to 1000 μg/L. For a Jet-A fuel sample doped with 143 μg/L Cu[EA] (Table 1), the initial, steady state absorbance values recorded prior to standard addition were the same for both the BCP-ascorbic acid and BCP-hydroquinone systems. The slopes of the two linear fits following standard addition were also very similar, suggesting similar kinetics with regards to the different reducing agents.

TABLE 1

| Reagents | Initial Absorbance | Slope (L/μg) | Obs./Cal BCP/GFAA (μg/L) |
|---|---|---|---|
| Jet-A doped with Cu (II) | | | |
| 2.0 mM HQ, 1.5 mM BCP, | 0.022 | 1.98E−4 | 145/143 |
| 2.0 mM AA, 1.5 mM BCP, NRL #02-01 (1/7 dilution) | 0.022 | 2.0E−4 | 142/143 |
| 2.0 mM HQ, 1.5 mM BCP | 0.022 | 2.06E−4 | 135/150 |
| 2.0 mM AA, 1.5 mM BCP | 0.025 | 2.08E−4 | 153/150 |
| 2.0 mM AA, 1.5 mM BCP, 8 mg/L MDA | 0.025 | 2.09E−4 | 151/150 |

As shown in Table 1, when the standard addition method was applied to JP-5 fuel samples containing copper from exposure to copper plates and alloy surfaces (samples #02-23 (not shown in table) and #02-01), the method consistently yielded low results when compared with GFAA analysis. By increasing the ethanol content to 20% and the sonication time to 15 minutes, however, the copper concentration was accurately determined with the BCP-ascorbic acid system, but not with BCP-hydroquinone. Note that prior to standard addition, the initial, steady state absorbance value recorded for the BCP-hydroquinone system (0.022) was lower than that observed for the BCP-ascorbic acid system (0.025). The slopes of the standard addition curves, on the other hand, were nearly identical. It was this initial difference in the steady state absorption levels that results in the negative errors observed for the BCP-hydroquinone assay of particular jet fuel samples. This suggested that a small fraction of the dissolved copper in these fuels is strongly complexed with fuel constituents, presumably various sulfur, nitrogen, and oxygen containing ligands, and is, therefore, inaccessible to the BCP-hydroquinone reagent system.

In order to accurately determine the total dissolved copper in fuel samples via this spectrophotometric approach, the analytical reagent mixture (BCP and reducing agent) had to successfully compete for copper complexation with native ligands present in these fuel samples. Thus, the reagents and conditions must be chosen to favor the formation of the BCP-Cu complex. Comparing the protonation constants of ascorbic acid ($pK_{a1}$ 11.35, $pK_{a2}$ 4.02) with hydroquinone ($pK_{a1}$ 11.39, $pK_{a2}$ 9.85), illustrated the fact that ascorbic acid is significantly more acidic in aqueous solution. Although these protonation constants did not describe the real acidities of these two reducing agents in a mixture of ethanol (dielectric constant 24.6) and jet fuel (dielectric constant~2.00), their relative acidities should remain almost unchanged. In addition to the reducing power of ascorbic acid for reducing Cu(II) to Cu(I), the acidity of ascorbic acid likely played an important role in destabilizing native copper complexes found in the jet fuel samples. As noted above, by increasing the ethanol content from 10% to 20%, the quantitative accuracy of the BCP method was improved, a result which was consistent with the proposed advantages afforded by the acidity of ascorbic acid under these conditions. As the ethanol content of the fuel mixture was increased, the dielectric constant also increased, favoring deprotonation of ascorbic acid and destabilization of any strong copper-fuel complexes.

Figure 7:
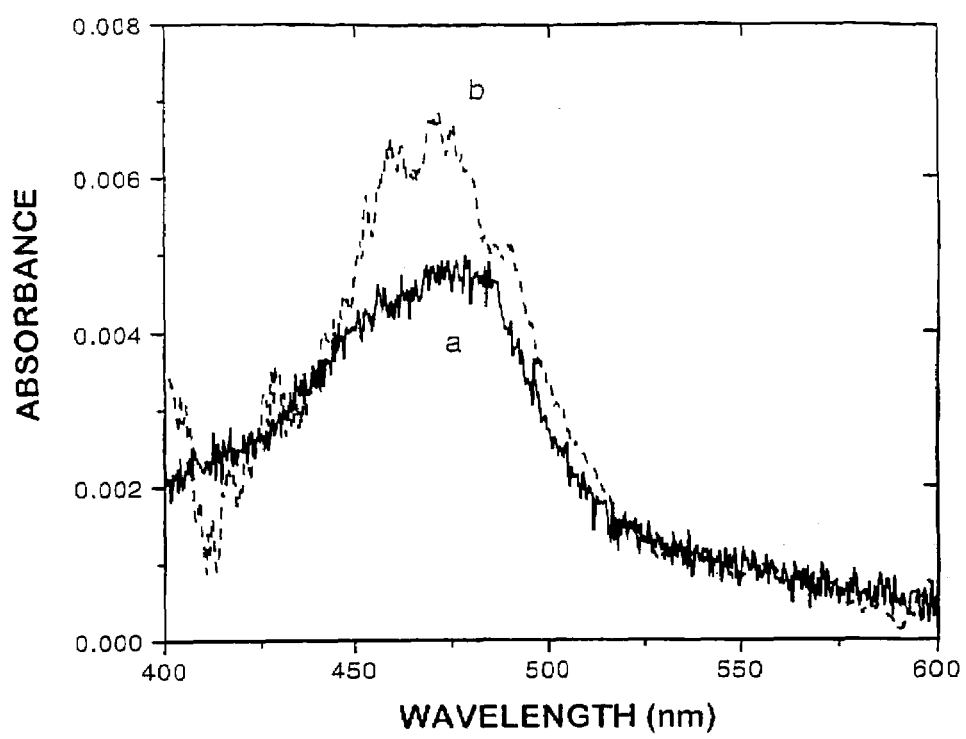
FIG. 7 shows a comparison of BCP response for a 26 µg/L copper in jet fuel sample using a) a benchtop spectrophotometer, and b) a portable, fiber optic spectrometer.
Figure 8:
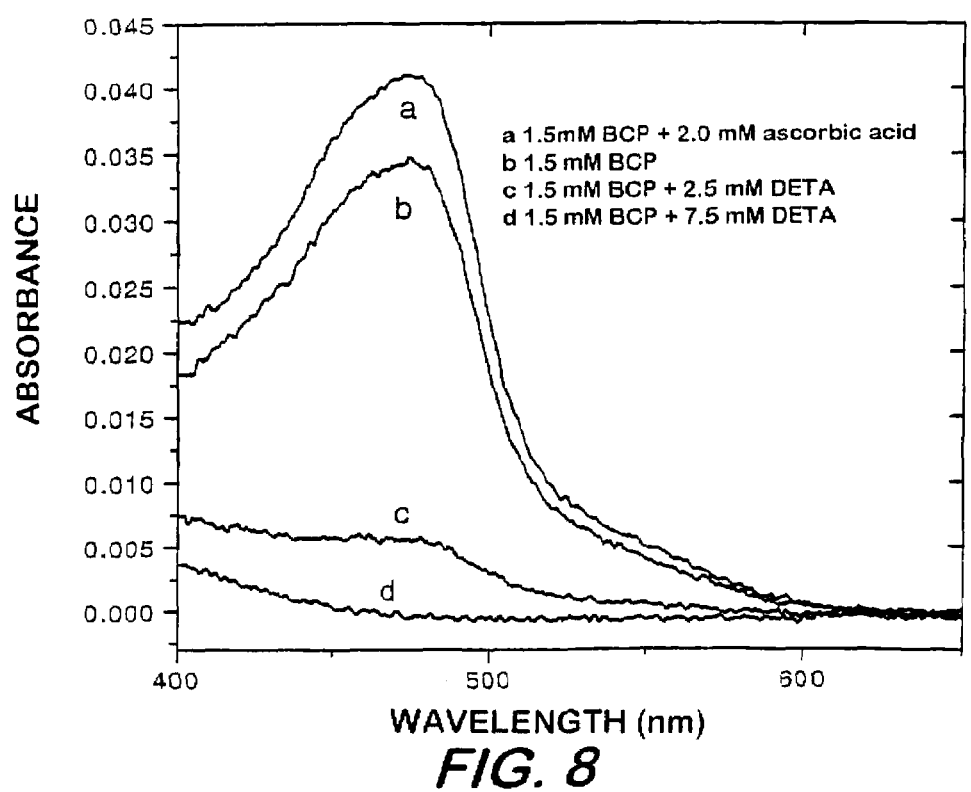
FIG. 8 shows spectrophotometric plots showing the ability of diethylenetriamine (DETA) to compete with BCP for the copper in JP-5 fuel #01-21 containing 200 µg/l copper from copper (II) ethylacetoacetate.

The optimal conditions derived for copper analysis, regardless of copper doping method or contamination history, were found to be $2.0 \times 10^{-3}$ M ascorbic acid, $1.5 \times 10^{-3}$ M BCP, 20% ethanol, and 15 minutes sonication. Table 2 compares the analytical results obtained for a number of different jet fuel samples analyzed by both the BCP-ascorbic acid method and GFAA, demonstrating excellent agreement between these two analytical techniques. FIG. 7 compares the sensitivity achieved for the detection of 26 μg/L copper in jet fuel by the BCP/ascorbic acid method using a benchtop spectrophotometer (6.2 μg/L detection limit) and a portable, fiber optic spectrometer (7.5 μg/L detection limit).

TABLE 2

| Sample | BCP-Ascorbic Acid Assay $Cu_{total}$ (μg/L) | GFAA $Cu_{total}$ (μg/L) |
|---|---|---|
| Dilutions of JP-5 #02-01 with #01-21 | | |
| 1/35* | 35(±4) | 36(±2) |
| 1/25 | 46(±3) | 48(±2) |
| 1/20 | 61(±5) | 57(±2) |
| 1/16 | 70(±4) | 70(±2) |
| 1/10 | 104(±3) | 107(±4) |
| 1/6 | 168(±6) | 174(±6) |
| Dilutions of JP-5 #02-23 with #01-21 | | |
| No dilution | 232(±8) | 224(±9) |
| No dilution (with 4 mg/l MDA) | 227(±2) | |
| 1/2 | 111(±3) | 112(±4) |
| 1/3 | 72(±4) | 75(±3) |
| Jet-A (Cu-free) + Cu[EA] | 105(±2) | 100(±5) |
| | 25(±4) | 26(±1) |
| JP-5 #02-23 after treatment with DETA to remove Cu | 32(±3) | 33(±2) |

*Fuel #02-01 was doped with copper from exposure to copper plates. Dilutions were obtained by mixing with JP-5 fuel #01-21, which is the same fuel without added copper. Fuel #02-23 was a JP-5 fuel from shipboard sampling. Cu[EA] = copper (II) ethylacetoacetate.

The active ingredient in the approved metal deactivating additive (MDA), N,N'-disalicylidine-1,2-propanediamine, is a hydroxyaromatic Schiff base ligand that forms a tetradentate complex with Cu(II) via two imino nitrogen atoms and two phenolic oxygen atoms. The MDA-Cu(II) complex has very high stability (logK~21 in water) and was, thus, expected to compete with ascorbic acid and BCP for Cu(II) complexation when present in jet fuel samples. A study was carried out to measure the dissolved copper concentration in the presence of 2-8 mg/L MDA. Results demonstrated that the sensitivity and accuracy of the BCP/ascorbic acid approach remained the same over the entire MDA concentration range from 0-8 mg/L. This result contrasts with that of NQSP, which did not compete as well with MDA, showing a 37% decrease in sensitivity in the presence of 2 mg/L MDA. The success of the BCP-ascorbic acid system in extracting copper from the copper-MDA complex in fuel is consistent with a mechanism in which ascorbic acid protonates the phenolic oxygen donors of MDA to destabilize the MDA-Cu complex, enabling the reduction of copper and its subsequent complexation with BCP.

Obviously, many modifications and variations of the present invention are possible in light of the above teachings. It is therefore to be understood that, within the scope of the appended claims, the invention may be practiced otherwise than as specifically described.

We claim:

1. A method of measuring the concentration of metal ions in a sample comprising the steps of:
   providing a sample comprising a nonpolar, liquid hydrocarbon, suspected of containing a metal ion;
   adding a spirobenzopyran dye to the nonpolar, liquid hydrocarbon;
      wherein the spirobenzopyran dye forms a complex with the metal ion in the nonpolar, liquid hydrocarbon;
      wherein the complex has a spectral shift in light absorbance relative to the spirobenzopyran dye;
   sonicating the sample;
   observing the spectral shift of the nonpolar, liquid hydrocarbon; and
   calculating the concentration of the metal ion in the nonpolar, liquid hydrocarbon.

2. The method of claim 1, wherein the nonpolar, liquid hydrocarbon comprises jet fuel.

3. The method of claim 1, wherein the metal ion is Cu(II).

4. The method of claim 1, wherein the nonpolar, liquid hydrocarbon comprises more than one metal ion.

5. The method of claim 1, wherein the spirobenzopyran dye is quinolinospiropyranindoline.

6. The method of claim 1, wherein the spirobenzopyran dye is nitroquinolinospiropyranindoline.

7. The method of claim 1, wherein a polar, organic solvent is added to the sample.

8. The method of claim 7, wherein the spirobenzopyran dye is dissolved in the solvent when the solvent is added to the sample.

9. The method of claim 7, wherein the solvent is ethanol.

10. The method of claim 9, wherein the concentration of ethanol in the nonpolar, liquid hydrocarbon after the adding step is at least about 2%.

11. The method of claim 7, where the observing step comprises measuring the absorbance spectrum of the spirobenzopyran dye dissolved in the solvent.

12. The method of claim 1, wherein the observing step comprises the step of measuring the absorbance spectrum of the nonpolar, liquid hydrocarbon after the adding step and one or more steps selected from the group consisting of measuring the absorbance spectrum of the nonpolar, liquid hydrocarbon before the adding step, measuring the absorbance spectrum of the spirobenzopyran dye, measuring the absorbance spectrum of the complex, and measuring the absorbance spectrum of a composition known to be free of the metal ion.

13. The method of claim 1, wherein the nonpolar, liquid hydrocarbon comprises a metal deactivating agent.

14. The method of claim 1, wherein the calculating step comprises principle component analysis.

15. The method of claim 1, wherein the method is capable of measuring about 9 ppb Cu(II) in jet fuel.

16. A method of measuring the concentration of copper ions in a sample comprising the steps of:
   providing a sample comprising a nonpolar, liquid hydrocarbon, suspected of containing a copper ion;
   adding bathocuproine and a reducing agent to the nonpolar, liquid hydrocarbon to create a spectral shift in light absorbance caused by complexation of the bathocuproine to the metal ion in the nonpolar, liquid hydrocarbon;

sonicating the sample;

observing the spectral shift of the nonpolar, liquid hydrocarbon; and calculating the concentration of the copper ion in the nonpolar, liquid hydrocarbon.

17. The method of claim 16, wherein the nonpolar, liquid hydrocarbon sample is jet fuel.

18. The method of claim 16, wherein the copper ion is selected from the group consisting of Cu(I), Cu(II), and mixtures thereof.

19. The method of claim 16, wherein the reducing agent is ascorbic acid.

20. The method of claim 16, wherein a polar, organic solvent is added to the sample.

21. The method of claim 20, wherein the bathocuproine is dissolved in the solvent when the solvent is added to the sample.

22. The method of claim 20, wherein the solvent is ethanol.

23. The method of claim 22, wherein the concentration of ethanol in the nonpolar, liquid hydrocarbon after the adding step is at least about 2%.

24. The method of claim 20, where the observing step comprises measuring the absorbance spectrum of the bathocuproine dissolved in the solvent.

25. The method of claim 16, wherein the observing step comprises the step of measuring the absorbance spectrum of the nonpolar, liquid hydrocarbon after the adding step and one or more steps selected from the group consisting of measuring the absorbance spectrum of the nonpolar, liquid hydrocarbon before the adding step, measuring the absorbance spectrum of the bathocuproine dye, measuring the absorbance spectrum of the complex, and measuring the absorbance spectrum of a composition known to be free of the metal ion.

26. The method of claim 16, wherein the nonpolar, liquid hydrocarbon comprises a metal deactivating agent.

27. The method of claim 16, wherein the method is of capable of measuring about 8 ppb total Cu(I) and Cu(II) in jet fuel.

28. A method of measuring the concentration of metal ions in a fuel sample comprising the steps of:

providing a sample comprising a fuel suspected of containing a metal ion;

adding a dye to the fuel;

wherein the dye forms a complex with the metal ion in the fuel;

wherein the complex has a spectral shift in light absorbance relative to the dye; sonicating the sample;

observing the spectral shift of the fuel; and calculating the concentration of the metal ion in the fuel.

29. The method of claim 28, wherein the fuel is ajet fuel.

30. The method of claim 28, wherein the metal ion is one or more copper ions.

* * * * *